United States Patent [19]

Ogura et al.

[11] 4,341,707

[45] Jul. 27, 1982

[54] IMIDO CARBONATE COMPOUND, PRODUCTION THEREOF AND USES THEREOF AS REAGENT FOR FORMING ACTIVE ESTER OF AMINO ACIDS

[75] Inventors: Haruo Ogura, 55, Jinyanae, Tokiwadaira, Matsudo-shi, Chiba-ken, Japan; Kazuyoshi Takeda, Yokohama, Japan

[73] Assignee: Haruo Ogura, Chiba, Japan

[21] Appl. No.: 141,365

[22] Filed: Apr. 18, 1980

[30] Foreign Application Priority Data

May 2, 1979 [JP] Japan ................................ 54-53347

[51] Int. Cl.³ ................ C07D 403/12; C07D 207/46; C07F 9/09; C07D 498/04
[52] U.S. Cl. ...................... 260/326 C; 260/112.5 R; 260/526 N; 260/326.26; 260/326.4; 260/326.5 A; 260/454; 546/113; 546/118; 548/165; 548/221; 548/305
[58] Field of Search ........... 260/326.26, 326 N, 326 C

[56] References Cited

U.S. PATENT DOCUMENTS 3,887,582 6/1975 Holub et al. .................. 260/326.26

FOREIGN PATENT DOCUMENTS 574953 4/1959 Canada ........................... 260/326 A

OTHER PUBLICATIONS

Anderson et al., J. Amer. Chem. Soc. 85, 3039 (1963).
Stepanoya et al., J. Gen. Chem. (USSR) 45, 2451–2453, (1976).

Gross et al., Angew. Chem. Int. Ed. 6, 570, (1967).
Itoh et al., Bull. Chem. Soc. Japan 47, 471 (1974).
Glatthard et al., Helv. Chim. Acta 46, 795 (1963).
Miyoshi, Bull. Chem. Soc. Japan 46, 1489–1496, (1973).
Schattenkert et al., Rec. Trav Pay–Bas 92, 92 (1973).

*Primary Examiner*—Mark L. Berch
*Attorney, Agent, or Firm*—Larson and Taylor

[57] ABSTRACT

A new carbonate compound which is N,N'-di-succinimidyl carbonate, N,N'-diphthalimidyl carbonate or N,N'-bis(5-norbornene-2,3-dicarboxyimidyl) carbonate is produced by reacting an N-hydroxy compound of the formula

R-OH 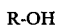

wherein R is succinimido, phthalimido or 5-norbornene-2,3-dicarboximido group, with a silylating agent, followed by reacting the resultant silylated product with phosgene, or alternatively by reacting said N-hydroxy compound with trichloromethyl chloroformate either in the molten state or in the presence of a non-polar organic solvent such as xylene. This new carbonate compound is useful not only as a reagent for forming active esters from amino acid but also as a reagent for introducing a carbonyl group between a pair of amino groups, a pair of amino and hydroxyl groups or a pair of amino and mercapto groups, for producing an isothiocyanate from a dithicarbamic acid by removal of hydrogen sulfide from the latter, and for producing acrylic acid derivatives from N-protected serine by dehydration of the latter.

4 Claims, No Drawings

IMIDO CARBONATE COMPOUND, PRODUCTION THEREOF AND USES THEREOF AS REAGENT FOR FORMING ACTIVE ESTER OF AMINO ACIDS

SUMMARY OF THE INVENTION

This invention relates to new carbonate compounds which are useful as a reagent for the conversion of amino acids into their active ester for use in synthesis of peptides. This invention also relates to processes for the production of these new carbonate compounds, and this invention further relates to various uses of the new carbonate compounds and more particularly for use in the preparation of active esters of amino acid and for use as a reagent for introducing carbonyl group or as a reagent for removing hydrogen sulfide or as a dehydrating agent.

BACKGROUND OF THE INVENTION

In the conventional synthesis of peptides, there is known the active ester method in which the amino acid is firstly converted into an active ester thereof and then condensed with a second amino acid. For the activation of an amino acid, it is generally known that the amino acid may be converted into its active ester, its acid anhydride or its acid azide which is subsequently reacted with a second amino acid. It is known that the active ester method as well as the acid anhydride method and the azide method are unlikely to involve an undesired racemization of the amino acid employed. When the synthesis of peptides is performed according to the active ester method, the process of condensing an amino acid with a second amino acid usually includes two stages, that is, the first stage of preparing an active ester of the amino acid and the second stage of coupling the amino acid active ester so prepared with an amine component (namely, the second amino acid having the free amino group which is to be condensed with the activated carboxylate group of the amino acid active ester so that the amido linkage is formed between these two amino acid reactants). It has been reported that when the later stage, that is, the coupling stage is effected according to the known "backing off" method, the undesired racemization is unlikely to occur. Accordingly, if the stage of activating the amino acid can be effected substantially without involving the racemization, it is feasible to carry out the fragment condensation of the two amino acid reactants in a favorable way without bringing about the racemization of the amino acids throughout the overall process of synthesizing the peptides from amino acids.

In general, it is known that the active ester group which can be used to convert an amino acid into its active ester form includes p-nitrophenyl group, N-hydroxysuccinimido group and N-hydroxyphthalimido group. As one of the common methods for the preparation of the active esters of an amino acid, there may be mentioned such method in which the amino acid is reacted with N-hydroxysuccinimide (hereinafter sometime abbreviated as HOSu) in the presence of dicyclohexylcarbodiimide (usually abbreviated as DCC) as a dehydrating agent to form the N-hydroxysuccinimide ester of the amino acid (Anderson et al "Journal of American Chemical Society" 85, 3039 (1963)). This DCC method enjoys many advantages that the resulting amino acid N-hydroxysuccinimide ester is highly crystalisable (and hence readily purifiable) and highly reactive, and that the N-hydroxysuccinimide liberated in the coupling stage is soluble in water and hence can be removed from the reaction mixture merely by washing with water after the coupling reaction is completed. However, it is also known that the DCC method suffers from some drawbacks that the DCC used as the dehydrating agent and the amino acid N-hydroxysuccinimide ester prepared are both oleophilic in their nature so that the removal of the DCC from the reaction mixture containing the desired amino acid active ester prepared cannot be achieved merely by extracting with an organic solvent but needs troublesome operations for the isolation of the desired amino acid active ester product; that β-alanine derivatives can be by-produced from the amino acid by Lossen-rearrangement under the action of DCC and HOSu; and that when the DCC method is applied to asparagine, glutamine or such another amino acids containing once an acid amido group in the molecule thereof, a nitrile derivative can undesirably by by-produced therefrom by dehydration under the action of DCC.

Further known methods for the preparation of the N-hydroxysuccinimide ester of an amino acid include such method in which trifluoroacetic acid anhydride is used and reacted with N-hydroxysuccinimide to form the N-hydroxysuccinimide ester of trichloroacetic acid which is then reacted with an amino acid to produce the active ester of the amino acid through the ester-interchange reaction (Stepanoya et al, "J. Gen. Chem." (USSR) 45, 2451 (1976)). When this prior art method is applied to N-t-butoxycarbonylglycine (Boc-Gly), the reactions involved therein may be shown by the following scheme:

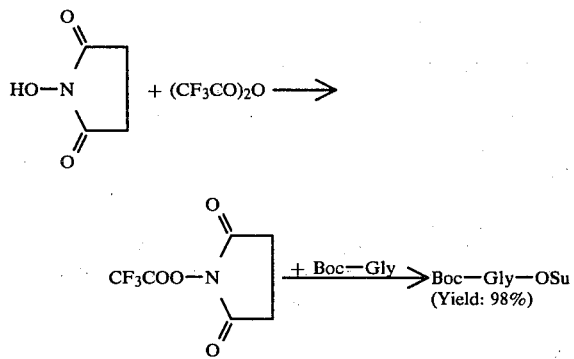

With this prior art method, however, the trichloroacetic acid N-hydroxysuccinimide ester obtained as the intermediate must be prepared just before its use and hence can neither be isolated nor be purified, so that the active ester of the amino acid obtained using the trichloroacetic acid N-hydroxysuccinimide ester needs repeated purifications. Besides, the reaction of preparing the intermediate trichloroacetic acid N-hydroxysuccinimide ester has to be carried out under absolutely anhydrous conditions, which provides a disadvantage, too.

According to Groos et al ("Agnew. Chem. Internt." Edit. 6, 570 (1967)), N-hydroxysuccinimide potassium salt is reacted with phosgene to prepare N-hydroxysuccinimide chloroformate which is then reacted with an N-protected amino acid in the presence of triethylamine to give a mixed acid anhydride. The mixed acid anhydride so prepared is subsequently heated to yield the N-hydroxysuccinimide active ester of the N-protected amino acid. When this method of Groos et al is applied to N-benzyloxycarbonylphenylalanine (Z-Phe), the reactions involved therein are shown by the following scheme:

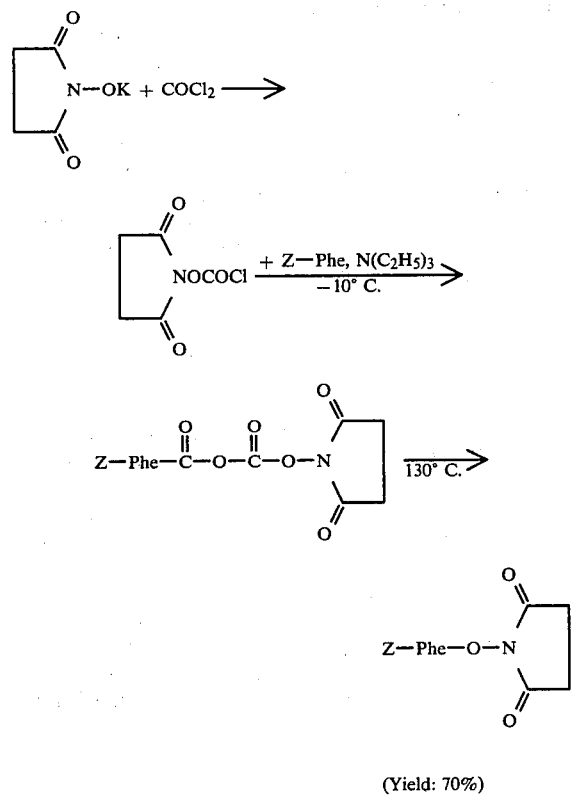

(Yield: 70%)

The method of Groos et al, however, can suffer from some disadvantages that the operations required in this method are complicated and that there involves a risk that the undesired racemization of the amino acids employed could take place due to the effect of chloride ions which would be formed during the reactions.

According to Ito ("Bull. Chem. Soc. Jpn." 47, 471 (1974)), there is proposed a method of activating an organic acid in which an organic acid such as benzoic acid is activated by reacting with an asymmetrical carbonate derivative, particularly ethyl 2-ethoxycarbonyloxyimino-2-cyanoacetate in the presence of diethylamine, as illustrated by the following scheme:

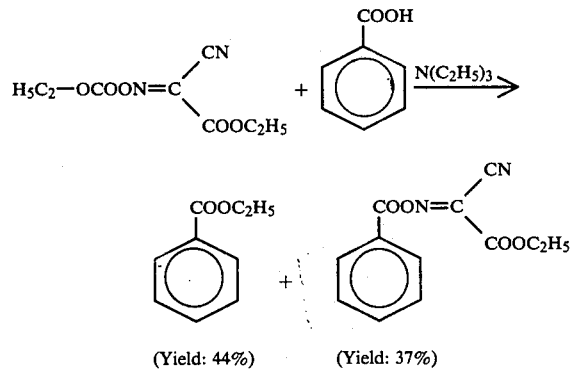

(Yield: 44%) (Yield: 37%)

With this method of Ito, it is to be noticed that two different esters can be formed concurrently due to the assymmetry of the carbonate derivative employed as the activating reagent, and that one of the two esters formed is the activated ester as desired but the other is not the activated ester. According to the method of Ito, it is also possible to employ ethyl 2-(p-nitrophenyloxy)-carbonyloxyimino-2-cyanoacetate as the activating assymmetrical carbonate derivative. When using this particular carbonate compound, an amino acid can be converted into its active ester in a yield of 50 to 60%. When this procedure according to the method of Ito is applied to N-benzyloxycarbonylphenylalanine (Z-Phe), the reactions involved therein may be shown by the following scheme:

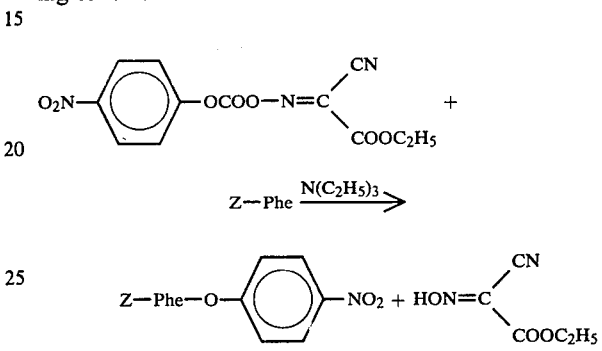

With this procedure, however, there is not obtained the desired active ester of the amino acid which is unlikely to involve racemization of the amino acid.

According to Glatthard et al ("Helv. Chem. Acta." 46, 795 (1963)), there is proposed a method for preparing an active ester of an amino acid in a favorable yield by reacting an amino acid with a diphenyl carbonate derivative which is formed by reaction of a certain phenol derivative with phosgene. When this diphenyl carbonate derivative is employed as the reagent of activating the amino acid, however, there involves a risk that the amino acid can undergo racemization in the stage of the aminolysis, that is, the stage where the activated amino acid ester is coupled with the amine component (i.e. the second amino acid) to produce the amido linkage.

DETAILED DESCRIPTION OF THE INVENTION

We, the present inventors, have now reviewed the above-mentioned various methods of the prior art for the preparation of the active ester of amino acids with taking into account the advantages and disadvantages of these prior art methods, and as a consequence, we have now attained an idea that such a compound which is in the form of an N-hydroxy derivative and also in the form of a symmetrical carbonate can successfully be employed as the reagent for converting an amino acid into its active ester which is to be used in the synthesis of peptides, and that if such compound is reacted with an amino acid, the preparation of the active ester from amino acid can be achieved in a facile way and with a relatively high efficiency under moderate reaction conditions.

Following this idea, we have extensively researched and have now succeeded in producing a new carbonate compound represented by the general formula (I):

wherein R denotes succinimido group, phthalimido group or 5-norbornene-2,3-dicarboxyimido group. We have further found that when this carbonate compound of the formula (I) is reacted with an amino acid, the amino acid active ester can, in fact, be prepared at ambient temperature in a facile way and in a high yield, that the racemization of the amino acid employed is unlikely to occur during the preparation of the active ester therefrom, and that racemization of the amino acid is unlikely to occur also when the amino acid active ester so prepared is condensed with a second amino acid for the synthesis of a peptide.

An object of this invention is to provide a new carbonate compound which is useful as the activating reagent for the preparation of an active ester from an amino acid and which has not or substantially has not the risk of bringing about the racemization of the amino acid in the preparation of the amino acid active ester and also in the process of synthetizing a peptide using the amino acid active ester so prepared. The other object of this invention is to provide a process for the production of such new carbonate compound which can be performed in a facile way and in a high yield. Another objects of this invention will be clear from the following descriptions.

According to a first aspect of this invention, therefore, there is provided as the new compound a carbonate compound of the formula (I):

wherein R represents succinimido group, phthalimido group or 5-norbornene-2,3-dicarboximido group.

When the new carbonate compound of this invention is employed for preparing the active ester from an amino acid, the amino acid active ester can advantageously be produced in a high yield and without involving the racemization of the amino acid used. Besides, the new carbonate compound of this invention is advantageous in that it liberates gaseous carbon dioxide when it is reacting with the amino acid to produce its active ester, so that the end point of the reaction of the new carbonate compound with the amino acid is detectable visually by observing whether the evolution of gaseous carbon dioxide is ceased or not. The new carbonate compound of this invention is easy to handle, as it is not irritative to the skin of the human. In contrast, dicyclohexylcarbodiimide (DCC) which is employed in the aforesaid DCC method is very irritative to the skin. In addition, the new carbonate compound of this invention liberates N-hydroxysuccinimide, N-hydroxyphthalimide or N-hydroxy-5-norbornene-2,3-dicarboxyimide when it has reacted with the amino acid with affording the amino acid active ester, and the N-hydroxysuccinimide, N-hydroxyphthalimide or N-hydroxy-5-norbornene-2,3-dicarboxyimide so liberated is soluble in water and hence is readily separatable from the reaction mixture merely by washing the reaction mixture with water. In contrast, DCC is not soluble in water. Accordingly, when the DCC method is adopted for preparing an active ester from an amino acid, the simple procedure of washing the reaction mixture of the DCC method with water does not serve for removing DCC from the reaction mixture.

According to a second aspect of this invention, there is also provided a process for the production of the new carbonate compound of the formula (I)

wherein R represents succinimido, phthalimido or 5-norbornene-2,3-dicarboximido group, which comprises either (i) reacting a compound of the formula (II)

wherein R is as defined above, with a silylating agent, followed by reacting the resultant silylated product with phosgene under anhydrous conditions, or (ii) reacting a compound of the formula (II)

wherein R is as defined above, with trichloromethyl chloroformate in the molten state or at an elevated temperature in the presence of a non-polar organic solvent.

In the process of this second aspect invention, the procedure (i) is conducted in such a manner that the starting N-hydroxy compound of the formula (II) is reacted with a known silylating agent such as trimethylsilyldiethylamine (abbreviated as TMS-DEA) and hexamethyl disilazane in the absence or presence of an organic solvent such as toluene, xylene to produce a silylated product which is formed through the replacement of the hydrogen atom of the hydroxyl group of the N-hydroxy compound of the formula (II) by the alkyl silyl group of the silylating agent employed. When TMS-DEA is employed as the silylating agent, the silylated product obtained may be represented by the formula:

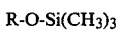

wherein R is defined above. The resulting silylated product is then reacted with phosgene ($COCl_2$) under ice-cooling in the presence of an organic solvent such as tetrahydrofuran (THF) under anhydrous conditions to give the desired carbonate compound of the aforesaid formula (I). The silylating agent available for this purpose is any one known for protecting organic acids and may, in general, be a tri-alkylsilyl di-alkyl amine of the general formula

wherein A is an alkyl group of 1–4 carbon atom and B is an alkyl group of 1–4 carbon atoms, or hexamethyldisilazane, N,O-bis(trimethylsilyl) acetamide, trimethylchlorosilane, N-trimethylsilyldiethylamine and N-trimethylsilylimidazole.

In the process of the second aspect invention, the procedure (ii) may be followed alternatively to the procedure (i). According to the procedure (ii), the N-hydroxy compound of the formula (II) is reacted with trichloromethyl chloroformate (TCF) either in such a manner that the two reactants are reacted with each other in the molten state, or in such a manner that the N-hydroxy compound of the formula (II) is reacted with TCF in an inert, non-polar organic solvent such as xylene at an elevated temperature e.g. of 100° C. to 150° C. and preferably at the refluxing temperature of the organic solvent employed.

When the process of this invention is conducted using N-hydroxysuccinimide of the formula:

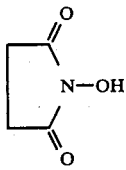

as the N-hydroxy compound of the formula (II), there is produced N,N'-disuccinimidyl carbonate (DSC) of the formula:

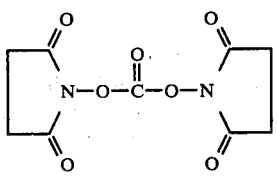

as the final compound of the formula (I).

When the process of this invention is conducted using N-hydroxyphthalimide of the formula:

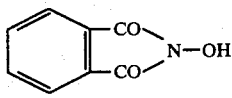

as the N-hydroxy compound (II), there is produced N,N'-diphthalimidyl carbonate of the formula:

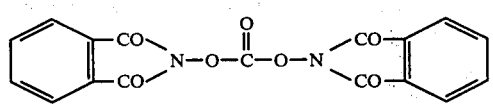

as the final compound (I).

When the process of this invention is performed using N-hydroxy-5-norbornene-2,3-dicarboximide of the formula:

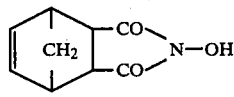

as the N-hydroxy compound (II), there is produced N,N'-bis(5-norbornene-2,3-dicarboximidyl)carbonate of the formula:

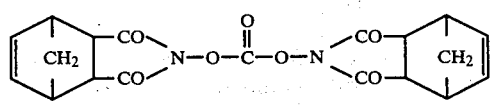

as the final compound (I).

The carbonate compound of the formula (I) according to this invention may be reacted easily with an N-protected amino acid at ambient temperature and at neutral or substantially neutral pH values to produce the corresponding N-protected amino acid active ester in a high yield. Evolution of gaseous carbon dioxide takes place during the reaction of the carbonate compound of this invention with the amino acid, so that the progress and the end point of the reaction can be detected visually by observing the evolution of the carbon dioxide gas. In addition, the desired amino acid active ester so produced can be obtained as a purified solution thereof simply by washing the reaction mixture with water, as the N-hydroxy compound of the formula (II) which was once liberated from the reaction of the carbonate compound of the formula (I) with the amino acid, as well as the unreacted carbonate compound (I) can be removed from the reaction mixture by the simple operation of washing with water. Besides, the amino acid active ester so produced may be used as such, namely without isolation and purification, to be reacted with a second amino acid in order to effect the aminolysis, that is, the formation of the amido linkage for the synthesis of a peptide. The new carbonate compound of the formula (I) according to this invention is also useful because it as such can act as the condensation agent which is employed directly in the synthesis of peptides from two or more amino acids, and hence the new compound (I) of this invention is very valuable as the reagent for use in the synthesis of peptides.

As stated in the above, the carbonate compound (I) of this invention is advantageously used as the reagent of forming the active ester of amino acid and also as the condensation agent for use in the synthesis of peptides. In order to demonstrate the advantageous uses of the new carbonate compound of this invention, we conducted some experiments of synthetizing peptides with using N,N'-disuccinimidyl carbonate (DSC) as a representative example of the carbonate compound (I) of this invention, reacting DSC with N-benzyloxycarbonylvaline (Z-Val); N-benzyloxycarbonylphenylalanine (Z-Phe); N-benzyloxycarbonylmethionine (Z-Met); N-t-butoxycarbonylglycine (Boc-Gly); N-t-butoxycarbonylvaline (Boc-Val); or N-t-butoxycarbonylphenylalanine (Boc-Phe) as one of the N-protected amino acids to produce the active ester of the respective N-protected amino acids, and further condensing these amino acid active esters (without being isolated from the reaction mixture) in pyridine with an amino acid ester which is used as the amine component, i.e., the second amino acid to be condensed with the above mentioned amino acid active ester and which is selected from glycine ethyl ester (Gly-OEt); leucine ethyl ester (Leu-OEt); and methionine ethyl ester (Met-OEt), for example. In these experiments, the yield and specific optical rotation $[\alpha]_D$ of the di-peptide products so synthetized were estimated and are shown in Table 1 below. For the comparison purpose, we investigated some literatures which have recorded how much were the yield and the value of the specific optical rotation shown by the corresponding di-peptides obtained when these were synthetized according to the DCC method of the prior art where the free N-hydroxysuccinimide (HOSu) was reacted with the N-protected amino acid in the presence of DCC to produce the amino acid active ester which was then, without isolation from the reaction mixture, condensed with the amino acid ethyl or methyl ester employed as the amine component. The literature we investigated with respect of the results of the DCC method is the "Rec. Trav. Pay-Bas" 92, 92 (1973). We further investigated the "Bull. Chem. Soc. Jpn." 46, 1489 (1973) as literature which has recorded the results of the synthesis of the di-peptides according to the method of the prior art using the N-acylated aziridinone as the dehydrating agent. The results obtained with these prior art methods are also summarized in Table 1 below.

TABLE 1

| N-Protected amino acid employed | Amine component employed | Di-peptides produced | Actual Yield (%) obtained | Yield (%) described in Literatures | Actual optical rotation $[\alpha]_D$ measured | Optical rotation $[\alpha]_D$ described in Literatures |
|---|---|---|---|---|---|---|
| Z—Val | Gly—OEt | Z—Val—Gly—OEt | 88 | 82 (a) | $[\alpha]_D^{25}$-27.3°(c 1.0, EtOH) | $[\alpha]_D^{20}$-27.0°(c 1.0, EtOH) (a) |
| Z—Phe | Gly—OEt | Z—Phe—Gly—OEt | 94 | 84 (a) | $[\alpha]_D^{24}$-18.5°(c 2.0, EtOH) | $[\alpha]_D^{20}$-17°(c 1.0, EtOH) (a) |
| Z—Phe | Leu—OEt | Z—Phe—Leu—OEt | 94 | — | $[\alpha]_D^{25}$-20.9°(c 1.0, EtOH) | — |
| Z—Phe | Met—OMe | Z—Phe—Met—OMe | 92 | — | $[\alpha]_D^{25}$-16.8°(c 1.0, EtOH) | — |
| Z—Met | Leu—OEt | Z—Met—Leu—OEt | 91 | — | $[\alpha]_D^{24}$-29.2°(c 1.0, EtOH) | — |
| Boc—Gly | Gly—OEt | Boc—Gly—Gly—OEt | 94 | — | — | — |
| Boc—Val | Leu—OEt | Boc—Val—Leu—OEt | 93 | — | $[\alpha]_D^{21}$-48.7°(c 1.0, EtOH) | — |
| Boc—Phe | Met—OMe | Boc—Phe—Met—OMe | 93 | 86 (b) | $[\alpha]_D^{22}$-12.1°(c 1.1, AcOH) | $[\alpha]_D$-11°(c 2.0, AcOH) (b) |
| Boc—Phe | Gly—OEt | Boc—Phe—Gly—OEt | 98 | — | $[\alpha]_D^{20}$-4.7°(c 1.0, dioxane) | — |

Notes:
Literature (a): M. Miyoshi, "Bull, Chem. Soc. Jpn." 46, 1489 (1973) which shows the results of the N-acylated aziridinone method.
Literature (b): C. Schattenkert, I. Voskuyl-Holtkamp. & R. Bokhorst. "Rec. Trav. Pay-Bas." 92, 92 (1973) which shows the results of the DCC method.

In our further researches, when N,N'-disuccinimidyl carbonate (DSC) as one of the new carbonate compound of this invention is reacted with amines, diamines, aminophenol, aminothiophenol and other some compounds in an inert organic solvent such as acetonitrile, it has been found that the reaction of introducing a carbonyl group between a pair of amino groups, a pair of amino and hydroxy groups or a pair of amino and mercapto groups takes place, with affording the corresponding urea derivatives or the corresponding carbonylated derivatives. Some examples of the carbonyl-introducing reactions with DSC are illustrated below with reference to the following schemes:

(i)
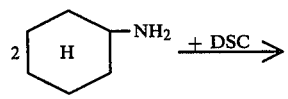

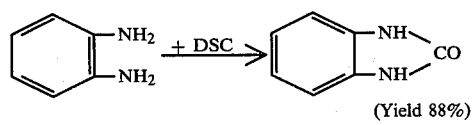
(Yield 100%)

(ii)
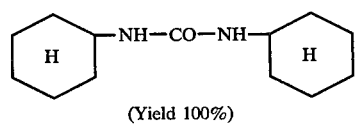
(Yield 88%)

(iii)
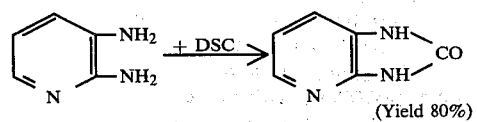
(Yield 80%)

(iv)
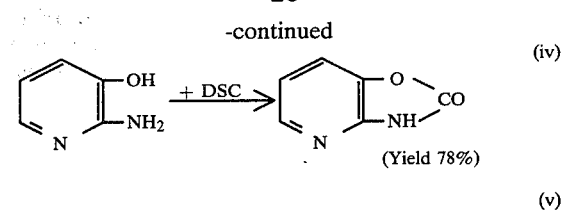
(Yield 78%)

(v)
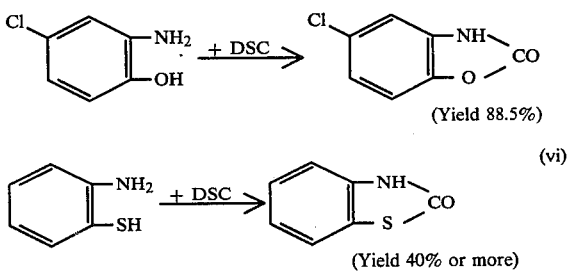
(Yield 88.5%)

(vi)
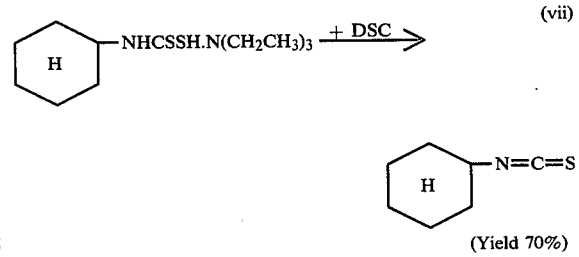
(Yield 40% or more)

Hithertofore, the above-mentioned reactions of introducing the carbonyl group was made using phosgene or carbonyl di-imidazole which is either toxic or expensive. In contrast to phosgene and carbonyl di-imidazole, DSC of this invention is less toxic, easy to handle and inexpensive as the reagent for introducing the carbonyl group.

Furthermore, it has been found that when a dithiocarbamic acid compound is reacted with DSC, it can be converted into an isocyanate compound by the removal of hydrogen sulfide from the former, as illustrated by the following scheme:

(vii)
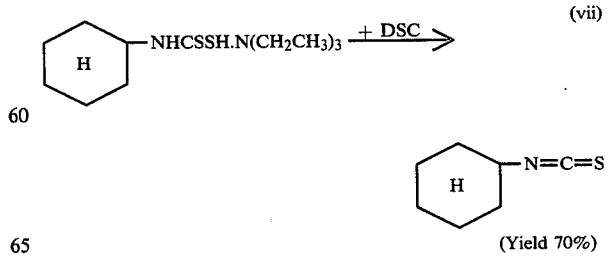
(Yield 70%)

Moreover, it has been found that when N-protected serine is reacted with two mol. of DSC, this amino acid undergoes simultaneously the esterification and dehydration to give the N-protected 2-aminopropenic acid N-succinimide ester, as shown by the following scheme:

(Yield 100%)

Furthermore, when N-hydroxysuccinimide (HOSu) is reacted with diphenylphospholyl chloride in dichloromethylene in the presence of triethylamine, N-succinimidyl diphenylphosphate (SDPP) is produced in a yield of 80% or more according to the following reaction equation:

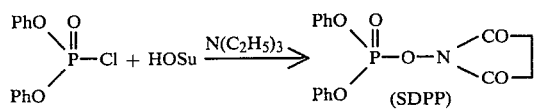

This SDPP is useful as the reagent for forming the active N-succinimide ester of amino acid, as it does not bring about the racemization of the amino acid employed. For instance, N-benzyloxycarbonylphenylalanine is reacted with SDPP in the presence of triethylamine to give N-benzyloxycarbonylphenylalanine N-succinimide ester in a yield of 100%. When an N-protected amino acid is reacted with an ethyl ester of a second amino acid in the presence of SDPP, a dipeptide is produced in a high yield by the coupling of these two amino acid reactants through the transesterification reaction without involving the racemization of the amino acids employed. For instance, N-benzyloxycarbonylvaline is reacted with glycine ethyl ester in the presence of SDPP and diethylamine to produce N-benzyloxyvalylglycine ethyl ester in a yield of 88%, as illustrated by the following scheme:

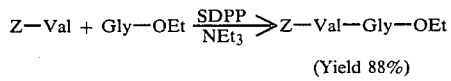

(Yield 88%)

This invention is now illustrated by the following Examples.

EXAMPLE 1

Production of N,N'-disuccinimidyl carbonate (DSC)

(1) 11.5 g (0.1 mol) of N-hydroxysuccinimide was admixed with 14.5 g (0.1 mol) of trimethylsilyldiethylamine (TMS-DEA) as a silylating agent, and the resultant admixture was heated for two hours under reflux. Subsequently, the unreacted TMS-DEA was distilled off from the reaction mixture which was then admixed with a volume of tetrahydrofuran (THF) and further with 100 ml of a solution of 30% (w/v) phosgene in toluene, under ice-cooling. The resultant admixture was stirred for five hours. The excess of phosgene and THF were then distilled off from the reaction solution, and the solid residue was washed with acetone to give a crystalline substance. Recrystallization from acetonitrile afforded 10.1 g of the titled compound in the form of colorless crystals. Yield 80% m.p. 211°~215° C.

IR. spectrum (cm$^{-1}$): $\nu_{-OCOO}^{KBr}$ 1750; $\nu^{KBr}$ 1840, 1780

NMR. spectrum (DMSO-α6, ppm.): 2.61 (8H. s -CH$_2$CH$_2$-×2)

Elemental analysis: Calcd. for C$_9$H$_8$O$_7$N$_2$: H 3.14, C 42.20, N 10.93%: Found: H 3.13, C 42.15, N 10.74%.

(2) 11.5 g (0.1 mol) of N-hydroxysuccinimide was admixed with 8.1 g of hexamethyldisilazane as a silylating agent and the resultant admixture was heated under reflux. After the reagents dissolved, the resultant solution was admixed with a volume of THF and with phosgene and subsequently processed in the same way as in the above procedure (1), to afford 8.5 g of the titled compound in the form of colorless crystals. Yield 65.9%.

(3) 11.5 g (0.1 mol) of N-hydroxysuccinimide was admixed with 6 ml (0.05 mol) of trichloromethyl chloroformate (TCF), and the resultant admixture was melted by heating. The heating was continued for 10 minutes and then the resultant melt was allowed to cool and to deposit a colorless crystalline material. This crystalline material was filtered off from the liquid phase and recrystallized from acetonitrile, affording 6.5 g of the titled compound in the form of colorless crystals. Yield 50%.

(4) 11.5 g (0.1 mol) of N-hydroxysuccinimide and 12 ml (0.1 mol) of TCF were added to a volume of xylene, and the mixture thus formed was heated under reflux. During the refluxing, a crystalline colorless material deposited. Six hours later, the crystalline material was filtered off and recrystallized from acetonitrile, affording 8.0 g of the title compound in the form of colorless crystals. Yield 80%.

EXAMPLE 2

The procedure of the Example 1 (1) was repeated except that N-hydroxyphthalimide (0.1 mol) was used in place of the N-hydroxysuccinimide. There was obtained N,N'-diphthalimidyl carbonate in the from of colorless crystals. m.p. 208°~210° C.

IR. spectrum (cm$^{-1}$): $\nu_{-NCO}^{KBr}$ 1850, 1790; $\nu_{-OCOO}^{KBr}$ 1740; $\nu_{-C_6H_5}^{KBr}$ 1600.

Elemental analysis: Calcd. for C$_{17}$H$_8$O$_7$N$_2$: C 59.38, H 4.20, N 7.29%: Found: C 59.11, H 4.14, N 7.29%.

EXAMPLE 3

The procedure of Example 1 (1) was repeated except that N-hydroxy-5-norbornene-2,3-dicarboximide (0.1 mol) was used in place of the N-hydroxysuccinimide. There was obtained N,N'-bis(5-norbornene-2,3-dicarboxyimidyl) carbonate in the form of colorless crystals. m.p. 242°~245° C. (with decomposition).

IR. spectrum (cm$^{-1}$): $\nu_{-NCO}^{KBr}$ 1850, 1790; $\nu_{-OCOO}^{KBr}$ 1750.

Elemental analysis: Calcd. for C$_{19}$H$_{16}$O$_7$N$_2$: C 57.97, H 2.29, N 7.95%: Found: C 57.97, H 2.35, N 8.10%.

EXAMPLE 4

This example illustrates the production of the active esters of various amino acids with use of DSC.

A solution of 0.251 g (0.001 mol) of N-benzyloxycarbonylvaline (Z-Val) 0.08 g (0.001 mol) of pyridine and 0.256 g (0.001 mol) of DSC in 10 ml of acetonitrile was stirred at ambient temperature for two hours, when bubbling of gaseous carbon dioxide ceased. Subsequently, the reaction solution was concentrated to a small volume and then admixed with ethyl acetate. The admixture (the solution) obtained was washed with aqueous 4% NaHCO$_3$, with an aqueous 1 N-HCl and with a saturated aqueous solution of NaCl to remove the liberated N-hydroxysuccinimide, followed by drying over anhydrous sodium sulfate. The solvent employed was distilled off from the solution, affording a colorless crystalline substance. Recrystallization of this crystalline substance from ethanol-petroleum ether gave 0.348 g of N-benzyloxycarbonylvaline N-succinimide ester (Z-Val-OSu) in the form of a colorless crystalline substance. Yield 100%.

A variety of amino acid active esters were prepared by the same procedure as above and some physical properties of them are summarized in Table 2 below. The results of elemental analysis of the active esters which were prepared in this Example but are already known from the disclosure in some literatures are not shown in Table 2.

TABLE 2

| Active ester formed | m.p. (°C.) | m.p.(°C.) described in Literature (a), (b) or (c) | IR (cm$^{-1}$, KBr) | | NMR (ppm)(CDCl$_3$) | | Elemental analysis |
|---|---|---|---|---|---|---|---|
| Z—Gly—OSu | 114–116 | 113–114(a) | 3300 | >NH | 2.85 | (4H.s.-CH$_2$CH$_2$) | — |
| | | | 1820 | } —N—CO— | 4.34 | (2H.d.-CH$_2$—Gly) | |
| | | | 1790 | | 5.19 | (2H.s.-CH$_2$—Z) | |
| | | | 1720 | >C=O | 5.20–5.32 | (1H.bd.-NH—) | |
| | | | 1690 | —OCONH— | 7.39 | (5H.s.-C$_6$H$_5$) | |
| | | | 1580 | C$_6$H$_5$ | | | |
| Z—Ala—OSu | 122–124 | 123–123.5(a) | 3250 | >NH | 1.58 | (3H.d.-CH$_3$) | — |
| | | | 1820 | } —NCO— | 2.82 | (4H.s.-CH$_2$CH$_2$—) | |
| | | | 1780 | | 4.78 | (1H.t.-CH—) | |
| | | | 1730 | >C=O | 5.18 | (2H.s.-CH$_2$—Z) | |
| | | | 1710 | —OCONH— | 5.20–5.49 | (1H.b.-NH—) | |
| | | | 1580 | —C$_6$H$_5$ | 7.39 | (5H.s.-C$_6$H$_5$) | |
| Z—Val—OSu | 115–117 | 116–117(a) | 3250 | >NH | 0.96,1.06 | (3H.two d.-CH$_3$) | — |
| | | | 1810 | } —N—CO— | 2.00–2.48 | (1H.b.-CH—Val) | |
| | | | 1780 | | 2.81 | (4H.s.-CH$_2$CH$_2$—) | |
| | | | 1725 | >C=O | 4.38–4.92 | (1H.b.-CH—) | |
| | | | 1710 | —OCONH— | 5.10 | (2H.s.-CH$_2$—Z) | |
| | | | 1580 | —C$_6$H$_5$ | 5.14 | (1H.b.-NH—) | |
| | | | | | 7.34 | (5H.s.-C$_6$H$_5$) | |
| Z—Leu—OSu | 120–121.5 | 116–117(a) | 3300 | >NH | 0.61–1.00 | (6H.m.-CH$_3$ × 2) | — |
| | | | 1820 | } —N—CO— | 1.42–1.85 | (3H.m.-CH$_2$CH—) | |
| | | | 1790 | | 4.32–4.91 | (1H.b-CH—) | |
| | | | 1735 | >C=O | 5.11 | (2H.s.-CH$_2$—) | |
| | | | 1700 | —OCONH— | 5.34–5.50 | (1H.d.-NH—) | |
| | | | 1590 | —C$_6$H$_5$ | 7.35 | (5H.s.-C$_6$H$_5$) | |
| Z—Pro—OSu | 88–90 | 90(a) | 1820 | } —N—CO— | 0.72–1.70 | (4H.m.-CH$_2$CH$_2$—Pro) | — |
| | | | 1785 | | 2.81 | (4H.s.-CH$_2$CH$_2$—Su) | |
| | | | 1730 | >C=O | 3.37–3.75 | (2H.m.-N—CH$_2$—) | |
| | | | 1700 | —OCONH— | 4.50–4.89 | (1H.m.-CH—) | |
| | | | 1590 | —C$_6$H$_5$ | 5.19 | (2H.d.-CH$_2$—Z) | |
| | | | | | 7.37 | (5H.s.-C$_6$H$_5$) | |
| Z—Phe—OSu | 137–138 | 140–140.5(a) | 3300 | >NH | 2.84 | (4H.s.-CH$_2$CH$_2$—) | — |
| | | | 1810 | } —N—CO— | 2.90–3.50 | (2H.m.-CH$_2$—Phe) | |
| | | | 1770 | | 4.80–5.20 | (1H.m.-CH—) | |
| | | | 1725 | >C=O | 5.10 | (2H.s.-CH$_2$—Z) | |
| | | | 1670 | —OCONH— | 5.22–5.48 | (1H.b.-NH—) | |
| | | | 1590 | —C$_6$H$_5$ | 7.29–7.31 | (10H.two s.-C$_6$H$_5$) | |

TABLE 2-continued

| Active ester formed | m.p. (°C.) | m.p.(°C.) described in Literature [a], [b] or [c] | IR (cm$^{-1}$, KBr) | | NMR (ppm)(CDCl$_3$) | | Elemental analysis | | |
|---|---|---|---|---|---|---|---|---|---|
| Z—Met—OSu | 101.5–103 | 101–102[a] | 3300 | $>$NH | 2.11 | (3H.s.-s-CH$_3$) | — | | |
| | | | 1820 1780 | $\Big\}$ —N—CO— | 2.21–2.39 2.59 | (2H.m.-CH$_2$—) (2H.bd.-CH$_2$—s) | | | |
| | | | 1740 | $>$C=O | 4.68–5.01 | (1H.m.-CH—) | | | |
| | | | 1690 | —OCONH— | 5.16 | (2H.s.-CH$_2$—Z) | | | |
| | | | 1590 | —C$_6$H$_5$ | 5.36–5.68 7.38 | (1H.bd.-NH—) (5H.s.-C$_6$H$_5$) | | | |
| Z—Glu—OSu | 121.5–123 | — | 3200 | $>$NH | 2.24–2.56 | (4H.m.-CH$_2$CH$_2$—) | Calcd. for C$_{17}$H$_{19}$O$_7$N$_3$ | | Found |
| | | | 1810 1770 | $\Big\}$ —N—CO— | 2.88 4.46–4.80 | (4H.s.-CH$_2$CH$_2$—Su) (2H.b.-CH—.—NH—) | H C | 5.06% 54.11% | 5.07% 54.25% |
| | | | 1720 | $>$C=O | 5.11 | (2H.s.-CH$_2$—Z) | N | 11.14% | 11.12% |
| | | | 1690 | —OCONH— | 6.00–7.24 7.38 | (2H.b.-NH$_2$) (5H.s.-C$_6$H$_5$) | | | |
| Boc—Gly—OSu | 163–167 | 168–170[a] | 3300 | $>$NH | 1.54 | (9H.s.CH$_3$ × 3) | — | | |
| | | | 1820 1780 | $\Big\}$ —N—CO— | 2.88 4.28 | (4H.s.-CH$_2$CH$_2$—) (2H.d.-CH$_2$—) | | | |
| | | | 1740 | $>$C=O | 4.75–5.22 | (1H.m.-NH—) | | | |
| | | | 1670 | —OCONH— | | | | | |
| Boc—Ala—OSu | 161–162 | 143–144[a] | 3300 | $>$NH | 1.48 | (9H.s.-CH$_3$ × 3) | — | | |
| | | | 1810 | $\Big\}$ —N—CO— | 1.60 | (3H.s.-CH$_3$Ala) | | | |
| | | | 1780 1720 | | 2.85 4.22–4.90 | (4H.s.-CH$_2$CH$_2$—) (1H.m.-CH—) | | | |
| | | | | $>$C=O | | | | | |
| | | | 1680 | —OCONH— | 4.98–5.35 | (1H.m.-NH—) | | | |
| Boc—Val—OSu | 121–124 | 128–129[a] | 3350 | $>$NH | 1.05,1.17 | (6H.two d.-CH$_3$ × 2) | — | | |
| | | | 1810 | $\Big\}$ —N—CO— | 1.56 | (9H.s.-CH$_3$ × 3.Boc) | | | |
| | | | 1780 1735 | | 1.90–2.65 2.90 | (1H.m.-CH—) (4H.s.-CH$_2$CH$_2$—) | | | |
| | | | | $>$C=O | | | | | |
| | | | 1710 | —OCONH— | 4.34–4.84 4.84–5.24 | (1H.m.-CH—) (1H.m.-NH—) | | | |
| Boc—Leu—OSu | 119–122 | 116[a] | 3350 | $>$NH | 0.99 | (6H.d.CH$_3$ × 2) | — | | |
| | | | 1815 | $\Big\}$ —N—CO— | 1.50 | (9H.s.CH$_3$ × 3 Boc) | | | |
| | | | 1785 1735 | | 1.40–1.94 2.82 | (3H.m.-CH$_2$CH$_2$—) (4H.s.-CH$_2$CH$_2$—) | | | |
| | | | | $>$C=O | | | | | |
| | | | 1710 | —OCONH— | 4.32–5.00 | (2H.b.-NH—.—CH—) | | | |
| Boc—Phe—OSu | 150–152 | 152–153[a] | 3390 | $>$NH | 1.41 | (9H.s.-CH$_3$ × 3) | — | | |
| | | | 1810 | $\Big\}$ —N—CO— | 2.80 | (4H.s.-CH$_2$CH$_2$—) | | | |
| | | | 1780 1730 | | 3.10–3.32 4.54–5.08 | (2H.m.-CH$_2$—) (2H.m.-NHCH—) | | | |
| | | | | $>$C=O | | | | | |
| | | | 1690 | —OCONH— | 7.29 | (5H.s.-C$_6$H$_5$) | | | |
| Boc—Met—OSu | 127–129 | 128–129[a] | 3390 | $>$NH | 1.49 | (9H.s.-CH$_3$ × 3) | — | | |

TABLE 2-continued

| Active ester formed | m.p. (°C.) | m.p.(°C.) described in Literature [a], [b] or [c] | IR (cm$^{-1}$, KBr) | | NMR (ppm)(CDCl$_3$) | | Elemental analysis | | |
|---|---|---|---|---|---|---|---|---|---|
| | | | 1810 | ⎫ —N—CO— | 1.95–2.38 | (2H.m.-CH$_2$—) | | | |
| | | | 1785 | ⎬ | 2.60 | (2H.d.-s-CH$_2$—) | | | |
| | | | 1735 | ⎭ >C=O | 2.82 | (4H.s.-CH$_2$CH$_2$—) | | | |
| | | | 1680 | —OCONH— | 4.50–5.00 | (1H.b.-CH—) | | | |
| | | | | | 5.09–5.38 | (1H.mb.-NH—) | | | |
| Boc—Lys(Z) —OSu | 94–96 | — | (film) 3300 | >NH | 1.42 | (9H.s.-CH$_3$ × 3) | Calcd. for C$_{23}$H$_{31}$O$_3$N$_3$ | | Found |
| | | | | | 1.51–1.98 | (6H.m.-(CH$_2$)$_3$—) | | | |
| | | | 1820 | ⎫ —N—CO— | 2.78 | (4H.s.-CH$_2$CH$_2$—Su) | H | 6.54% | 6.67% |
| | | | 1785 | ⎬ | 2.91–3.39 | (2H.m.-NCH$_2$—) | C | 57.85% | 57.83% |
| | | | 1730 | ⎭ >C=O | 4.22–4.81 | (1H.b.-CH—) | N | 8.81% | 8.52% |
| | | | 1705 | —OCONH— | 5.10 | (2H.s.-CH$_2$—) | | | |
| | | | 1590 | —C$_6$H$_5$ | 5.15–5.43 | (2H.m.-NH— × 2) | | | |
| | | | | | 7.32 | (5H.s.-C$_6$H$_5$) | | | |
| Boc—Ser(Bzl) —OSu | Oil | — | (film) 3300 | >NH | 1.48 | (9H.s.-CH$_3$ × 3) | Calcd. for C$_{19}$H$_{24}$O$_7$N$_2$ | | Found |
| | | | | | 2.81 | (4H.s.-CH$_2$CH$_2$—) | | | |
| (Bzl = benzyl group) | | | 1820 | ⎫ —N—CO— | 3.90 | (2H.t.-CH$_2$—Ser) | H | 6.17% | 6.39% |
| | | | 1785 | ⎬ | 4.60 | (2H.s.-CH$_2$—Bzl) | C | 58.15% | 58.18% |
| | | | 1730 | ⎭ >C=O | 4.70–4.92 | (1H.b.-CH—) | N | 7.14% | 6.95% |
| | | | 1705 | —OCONH— | 5.22–5.40 | (1H.b.-NH—) | | | |
| | | | 1590 | —C$_6$H$_5$ | 7.32 | (5H.s.-C$_6$H$_5$) | | | |
| Z—Ala—Gly—OSu —OSu | 115–118 | 128–129[b] | 3300 | >NH | 1.38 | (3H.d.-CH$_3$) | Calcd. for C$_{17}$H$_{19}$O$_7$N$_3$ | | Found |
| | | | 1820 | ⎫ —N—CO— | 2.80 | (4H.s.-CH$_2$CH$_2$—) | H | 5.08% | 5.08% |
| | | | 1780 | ⎬ | 4.16–4.61 | (3H.m.-CH—,—CH$_2$—) | C | 54.11% | 54.11% |
| | | | 1730 | ⎭ >C=O | 5.10 | (2H.s.-CH$_2$—Z) | N | 11.14% | 10.98% |
| | | | 1700 | —OCONH— | 5.62 | (1H.d.-NH—urethane) | | | |
| | | | 1520 | —C$_6$H$_5$ | 7.07 | (1H.b.-NH—amido) | | | |
| | | | | | 7.35 | (5H.s.-C$_6$H$_5$) | | | |
| Z—Ala—Ala—OSu | 143–145 | 145–146[c] | 3300 | >NH | 1.50, 1.36 | (6H.two d.-CH$_3$ × 2) | Calcd. for C$_{18}$H$_{21}$O$_7$N$_3$ | | Found |
| | | | 1820 | ⎫ —N—CO | 2.75 | (4H.s.-CH$_2$CH$_2$—) | H | 5.41% | 5.44% |
| | | | 1780 | ⎬ | 4.00–4.49 | (1H.b.-CH—) | C | 55.24% | 54.69% |
| | | | 1730 | ⎭ >C=O | 4.50–5.32 | (1H.b.-CH—) | N | 10.74% | 10.46% |
| | | | 1700 | —OCONH— | 5.08 | (2H.s.-CH$_2$—) | | | |
| | | | 1520 | —C$_6$H$_5$ | 5.50 | (1H.bd.-NH—urethane) | | | |
| | | | | | 6.88 | (1H.bd,—NH—.amido) | | | |
| | | | | | 7.33 | (5H.s.-C$_6$H$_5$) | | | |
| Z—Ala—Phe—OSu | 136–138 | 136[c] | 3300 | >NH | 1.24 | (3H.d.-CH$_3$) | Calcd. for C$_{24}$H$_{25}$O$_7$N$_3$ | | Found |
| | | | 1820 | ⎫ —N—CO | 2.75 | (4H.s.-CH$_2$CH$_2$—) | H | 5.39% | 5.36% |
| | | | 1795 | ⎬ | 3.10–3.34 | (2H.m.-CH$_2$.Phe) | C | 61.66% | 61.40% |
| | | | 1740 | ⎭ >C=O | 3.94–4.43 | (1H.m.-CH—Ala) | N | 8.98% | 8.98% |
| | | | 1710 | —OCONH— | 4.95–5.60 | (2H.m.-NHCH—) | | | |
| | | | 1675 | —NHCO— | 5.04 | (2H.s.-CH$_2$—Z) | | | |
| | | | | | 6.84 | (1H.bd.-NH—amido) | | | |
| | | | | | 7.25, 7.35 | (10H.two s.-C$_6$H$_5$) | | | |
| Boc—Phe—Val— OSu | — | | 3300 | >NH | 1.00 | (6H.d.CH$_3$ × 2) | | | |

TABLE 2-continued

| Active ester formed | m.p. (°C.) | m.p.(°C.) described in Literature [a], [b] or [c] | IR (cm$^{-1}$, KBr) | | NMR (ppm)(CDCl$_3$) | | Elemental analysis |
|---|---|---|---|---|---|---|---|
| | | | 1820 1790 1740 | $\big\}$ —N—CO $>$C=O | 1.42 1.98–2.58 2.82 | (9H.s.CH$_3$ × 3) (1H.m.-CH—) (4H.s.-CH$_2$CH$_2$—) | |
| | | | 1680 1660 1600 | —OCONH— —NHCO— —C$_6$H$_5$ | 3.09 4.05–4.59 4.72–5.10 5.10–5.20 6.32–6.71 7.24 | (2H.d.-CH$_2$—) (1H.m.-CH—Phe) (1H.m.-CH—Val) (1H.m.-NH—) (1H.m.-NH—amido) (5H.s.-C$_6$H$_5$) | |

Notes:
Literature [a]: G. W. Anderson, J. E. Zimmerman and F. M. Callahan, "J. Amer. Chem. Soc.", 86, 1839 (1964).
Literature [b]: R. Fairweather and J. H. Jones, "J. Chem. Soc.", Perkin I. 1908 (1972).
Literature [c]: H. R. Bosshard, I. Schechter and A. Berger, "Helv. Chem. Acta.", 56, 717 (1973).

EXAMPLE 5

This example illustrates the synthesis of dipeptides with use of DSC.

A solution of 0.265 g (0.001 mol) of N-t-butoxycarbonylphenylalanine (Boc-Phe), 0.08 g (0.001 mol) of pyridine and 0.256 g (0.001 mol) of DSC in 10 ml of acetonitrile was stirred at ambient temperature. After thin-layer chromatography (TLC.) on silica gel slowed that Boc-Phe (the free acid form) disappeared in the solution, the reaction solution was admixed with a solution of 0.139 g (0.001 mol) of glycine ethyl ester hydrochloride (Gly-OEt.HCl) and 0.101 g (0.001 mol) of triethylamine in 10 ml of acetonitrile. 24 Hours later, the reaction mixture was concentrated to a small volume, and the concentrated solution was admixed with ethyl acetate, and then washed with aqueous 4% NaHCO$_3$, with aqueous 10% citric acid (or 1 N-hydrochloric acid) and finally with a saturated aqueous solution of sodium chloride to remove the liberated N-hydroxysuccinimide, followed by drying over sodium sulfate. The solvents employed were distilled off from the solution, leaving the dipeptide product as a colorless crystalline material. Recrystallization of this crystalline substance from ether-petroleum ether gave 0.342 g of the dipeptide (Boc-Phe-Gly-OEt) in the form of a colorless crystalline substance. Yield 97.7%.

A variety of dipeptides were prepared in the same way as mentioned above and some physical constants of them are shown in Table 3 below.

TABLE 3

| Dipeptide formed | m.p.(°C.) | m.p.(°C.) described in Literature [a] or [b] | IR (cm$^{-1}$; KBr) | | NMR (ppm. CDCl$_3$) | | Elemental analysis | | |
|---|---|---|---|---|---|---|---|---|---|
| Z—Val—Gly—OEt | 160–163 | 162–164[a] | 3250 | $>$NH | 0.89,1.00 | (6H.dd.-CH$_3$ × 2) | | Calcd. for | |
| | | | 1680 1640 1720 | —OCONH— —CONH— $>$C=O | 1.26 1.96–2.47 4.00 | (3H.t.-CH$_3$ 7Hz) (1H.m.-CH—) (2H.d.-CH$_2$—Gly) | H C N | C$_{17}$H$_{24}$O$_5$N$_2$ 7.19% 60.70% 8.33% | Found 7.14% 60.69% 8.15% |
| | | | 1550 | —C$_6$H$_5$ | 4.20 4.50–4.75 5.12 5.31–5.60 6.40–6.79 7.38 | (2H.q.-CH$_2$—7Hz) (1H.b.-CH—) (2H.s.-CH$_2$—Z) (1H.md.-NH—) (1H.b.-NH—amide) (5H.s.-C$_6$H$_5$) | | | |
| Z—Phe—Gly—OEt | 106–109 | 109–111[a] | 3250 | $>$NH | 1.19 | (3H.t.-CH$_3$ J = 7Hz) | | Calcd. for | |
| | | | 1720 | $>$C=O | 3.05 | (2H.d.-CH$_2$—Phe) | | C$_{21}$H$_{24}$O$_5$N$_2$ | Found |
| | | | 1680 1640 1590 | —OCONH— —CONH— —C$_6$H$_5$ | 3.92 4.17 4.26–4.75 5.04 5.58 6.42–6.74 7.12–7.29 | (2H.d.-CH$_2$—Gly) (2H.q.-CH$_2$—J = 7Hz) (1H.m.-CH—) (2H.s.-CH$_2$—Z) (1H.d.-NH— urethane) (1H.m.-NH—amide) (10H two s.-C$_6$H$_5$ × 2) | H C N | 6.29% 65.61% 7.28% | 6.23% 65.61% 7.15% |
| Z—Phe—Leu—OEt | 116–118 | — | 3250 | $>$NH | 0.89 | (6H.dd.-CH$_3$ × 2 Leu) | | Calcd. for C$_{25}$H$_{32}$O$_5$N$_2$ | Found |

TABLE 3-continued

| Dipeptide formed | m.p.(°C.) | m.p.(°C.) described in Literature [a] or [b] | IR (cm$^{-1}$; KBr) | | NMR (ppm. CDCl$_3$) | | Elemental analysis | | |
|---|---|---|---|---|---|---|---|---|---|
| | | | 1710 | $>$C=O | 1.24 | (3H.t.-CH$_3$ J = 7Hz) | H | 7.32% | 7.31% |
| | | | 1680 | —OCONH— | 1.34–1.64 | (3H.m.-CH$_2$CH—) | C | 68.16% | 68.31% |
| | | | 1640 | —CONH— | 3.04 | (2H.d.-CH$_2$—Phe) | N | 6.35% | 6.35% |
| | | | 1590 | —C$_6$H$_5$ | 4.15 | (2H.q.-CH$_2$—J = 7 Hz) | | | |
| | | | | | 4.38–4.75 | (2H.m.-CH— × 2) | | | |
| | | | | | 5.08 | (2H.s.-CH$_2$—Z) | | | |
| | | | | | 5.51 | (1H.d.-NH—urethane) | | | |
| | | | | | 6.46 | (1H.d.-NH—amide) | | | |
| | | | | | 7.21–7.32 | (10H.two s.-C$_6$H$_5$ × 2) | | | |
| Z—Phe—Met—OMe | 122–126 | — | 3300 | $>$NH | 1.82–2.60 | (4H.m.-CH$_2$CH$_2$—) | Calcd. for | | |
| | | | 1700 | | 2.04 | (3H.s.-s CH$_3$) | C$_{23}$H$_{28}$O$_5$N$_2$S | Found | |
| | | | | $>$C=O | | | | | |
| | | | 1680 | —OCONH— | 3.11 | (2H.d.-CH$_2$—Phe) | H | 6.34% | 6.33% |
| | | | 1650 | —CONH— | 3.74 | (3H.s.-CH$_3$) | C | 62.14% | 62.27% |
| | | | 1550 | —C$_6$H$_5$ | 4.28–4.75 | (2H.m.-CH— × 2) | N | 6.30% | 6.30% |
| | | | | | 5.11 | (2H.s.-CH$_2$—) | | | |
| | | | | | 5.20–5.50 | (1H.m.-NH—) | | | |
| | | | | | 6.33–6.62 | (1H.m.-NH—amide) | | | |
| | | | | | 7.24–7.34 | (10H.two s.-C$_6$H$_5$ × 2) | | | |
| Z—Met—Leu—OEt | 78–79 | — | 3270 | $>$NH | 0.91 | (6H.d.-CH$_3$ × 2 Leu) | Calcd. for C$_{21}$H$_{32}$O$_5$N$_2$S | Found | |
| | | | 1720 | $>$C=O | 1.28 | (3H.t.-CH$_3$ J = 7Hz) | H | 7.59% | 7.59% |
| | | | 1680 | —OCONH— | 1.48–1.76 | (3H.m.-CH$_2$CH—) | C | 59.41% | 59.34% |
| | | | 1640 | —CONH— | 1.76–2.22 | (2H.m.-CH$_2$—Met) | N | 6.59% | 6.62% |
| | | | 1590 | —C$_6$H$_5$ | 2.10 | (3H.s.-s-CH$_3$) | | | |
| | | | | | 2.42–2.78 | (2H.m.-s-CH$_2$—) | | | |
| | | | | | 4.19 | (2H.q.-CH$_2$— J = 7Hz) | | | |
| | | | | | 4.30–4.70 | (2H.m.-CH— × 2) | | | |
| | | | | | 5.12 | (2H.s.-CH$_2$—Z) | | | |
| | | | | | 5.60 | (1H.d.-NH—) | | | |
| | | | | | 6.58 | (1H.d.-NH—) | | | |
| | | | | | 7.38 | (5H.s.-C$_6$H$_5$) | | | |
| Boc—Gly—Gly—OEt | Oil | — | 3300 | $>$NH | 1.49 | (9H.s.-CH$_3$ × 3) | Calcd. for C$_{11}$H$_{20}$O$_5$N$_2$ | Found | |
| | | | 1750 | $>$C=O | 1.29 | (3H.t.-CH$_3$ J = 7Hz) | H | 7.74% | 7.73% |
| | | | 1700 | —OCONH— | 3.86 | (2H.d.-CH$_2$—Gly) | C | 50.75% | 50.48% |
| | | | 1650 (film) | —CONH— | 4.05 | (2H.d.-CH$_2$—Gly) | N | 10.76% | 10.55% |
| | | | | | 4.22 | (2H.q.-CH$_2$— J = 7Hz) | | | |
| | | | | | 5.29–5.66 | (1H.m.-NH—urethane) | | | |
| | | | | | 6.70–7.14 | (1H.m.-NH—amide) | | | |
| Boc—Val—Leu—OEt | 100–104 | — | 3300 | $>$NH | 0.49–1.00 | (12H.dd.-CH$_3$ × 4) | Calcd. for C$_{18}$H$_{34}$O$_5$N$_2$ | Found | |
| | | | 1750 | $>$C=O | 1.24 | (3H.t.-CH$_3$ J = 7Hz) | H | 9.56% | 9.48% |
| | | | 1680 | —OCONH— | 1.48 | (9H.s.-CH$_3$ × 3) | C | 60.30% | 60.07% |
| | | | 1640 | —CONH | 1.50–1.74 | (3H.m.-CH$_2$CH$_2$—) | N | 7.81% | 7.69% |
| | | | | | 1.82–2.34 | (1H.m.-CH—Val) | | | |
| | | | | | 3.69–4.80 | (2H.m.-CH— × 2) | | | |
| | | | | | 4.18 | (2H.q.-CH$_2$— J = 7Hz) | | | |
| | | | | | 4.92–5.35 | (1H.m.-NH—urethane) | | | |
| | | | | | 6.20–6.54 | (1H.m.-NH—amide) | | | |
| Boc—Phe—Met—OMe | 81–85 | 85[b] | 3300 | $>$NH | 1.41 | (9H.s.-CH$_3$ × 3) | | | |

TABLE 3-continued

| Dipeptide formed | m.p.(°C.) | m.p.(°C.) described in Literature (a) or (b) | IR (cm⁻¹; KBr) | | NMR (ppm. CDCl₃) | | Elemental analysis | | |
|---|---|---|---|---|---|---|---|---|---|
| | | | 1750 | $>$C=O | 1.71–2.20 | (2H.m.-CH₂-s-) | | | |
| | | | 1680 | —OCONH— | 2.02 | (3H.m.-s-CH₃) | | | |
| | | | 1640 | —CONH— | 2.26–2.60 | (2H.m.-CH₂—Met) | | | |
| | | | | | 3.04 | (2H.d.-CH₂—Phe) | | | |
| | | | | | 3.71 | (3H.s.-o-CH₂—) | | | |
| | | | | | 4.14–4.80 | (2H.m.-CH— × 2) | | | |
| | | | | | 4.82–5.18 | (1H.m.-NH—) | | | |
| | | | | | 6.38–6.66 | (1H.m.-NH—amide) | | | |
| | | | | | 7.24 | (5H.s.-C₆H₅) | | | |
| Boc—Phe—Gly—OEt | 90–92 | — | 3300 | $>$NH | 1.30 | (3H.t.-CH₃ J = 7Hz) | Calcd. for C₁₈H₂₆O₅N₂ | | Found |
| | | | 1740 | $>$C=O | 1.46 | (9H.s.-CH₃ × 3) | H | 7.48% | 7.55% |
| | | | 1690 | —OCONH— | 3.11 | (2H.bd.-CH₂—Phe) | C | 61.69% | 61.70% |
| | | | 1650 | —CONH— | 4.00 | (2H.d.-CH₂—Gly) | N | 8.00% | 7.96% |
| | | | 1600 | —C₆H₅ | 4.23 | (2H.q.-CH₂— J = 7Hz) | | | |
| | | | | | 4.32–4.70 | (2H.m.-CH— × 2) | | | |
| | | | | | 5.21 | (1H.d.-NH—) | | | |
| | | | | | 6.48–6.82 | (1H.m.-NH—amide) | | | |

Notes:
Literature (a): M. Miyoshi, "Bull, Chem. Soc. Jpn.", 46, 1489 (1973).
Literature (b): C. S. Schattenkert, I. Voskyl-Haltkamp and R. Bokhorst, "Rec. Trav. Chem. Pay-Bas", 92, 92 (1973).

Elemental analysis of the dipeptides which were prepared in this Example but are known from the literatures was omitted.

EXAMPLE 6

This example illustrates the synthesis of a variety of dipeptides.

(A) A solution of 0.223 g (0.001 mol) of N-benzyloxycarbonyl alanine (Z-Ala), 0.08 g (0.001 mol) of pyridine and 0.256 g (0.001 mol) of DSC in 10 ml of acetonitrile was stirred at ambient temperature. After silica gel TLC. showed that Z-Ala (the free acid form) disappeared in the solution, the reaction solution was concentrated to a small volume, and the concentrated solution was admixed with ethyl acetate and then washed with aqueous 4% NaHCO₃, with 1 N-HCl and finally with a saturated aqueous solution of sodium chloride to remove the liberated N-hydroxysuccinimide. The solution so treated was distilled to remove the ethyl acetate. The resultant solid residue was admixed with a solution of 0.165 g (0.001 mol) of phenylalanine (Phe-OH) and 0.101 g (0.001 mol) of triethylamine in 20 ml of a mixed solvent of acetonitrile and water (4:6 by volume). 24 Hours later, the reaction solution was concentrated to a small volume, and the concentrated solution was admixed with ethyl acetate, washed with aqueous 4% NaHCO₃, with 1 N-HCl and with a saturated aqueous solution of sodium chloride, followed by drying over anhydrous sodium sulfate. The dried solution was then filtered and the filtrate was distilled, affording a colorless crystalline substance. Recrystallization of this crystalline substance from methylene chloride-ethyl ether gave 0.34 g of N-benzyloxycarbonylalanyl-phenylalanine (Z-Ala-Phe-OH) as a colorless crystalline substance. Yield 90%.

(B) A solution of 0.223 g (0.001 mol) of N-benzyloxycarbonylalanine (Z-Ala), 0.08 g (0.001 mol) of pyridine and 0.256 g (0.001 mol) of DSC in 10 ml of dimethylformamide (DMF) was stirred at ambient temperature. After silica gel TLC. showed that Z-Ala (the free acid form) disappeared in the solution, the reaction solution was admixed with ethyl acetate and washed with aqueous 4% NaHCO₃, with 1 N-HCl and with a saturated aqueous solution of sodium chloride. The solution so treated was then distilled to remove the ethyl acetate, leaving a solid residue. This residue was admixed with a solution of 0.165 g (0.001 mol) of phenylalanine (Phe-OH) and 0.101 g (0.001 mol) of triethylamine in 20 ml of DMF, and the admixture so obtained was stirred at ambient temperature for 24 hours. Subsequently, the resultant reaction mixture was admixed with ethyl acetate, washed with aqueous 4% NaHCO₃, with 1 N-HCl and with a saturated aqueous solution of sodium chloride to remove the liberated N-hydroxysuccinimide, followed by drying over anhydrous sodium sulfate. The dried solution was filtered and the filtrate was distilled to remove the solvent, affording a colorless crystalline substance. Recrystallization of this crystalline substance from methylene chloride-ethyl ether gave 0.321 g of N-benzyloxycarbonylalanyl-phenylalanine (Z-Ala-Phe-OH) as a colorless crystalline substance. Yield 86%.

(C) A solution of 0.223 g (0.001 mol) of Z-Ala, 0.08 g (0.001 mol) of pyridine and 0.256 g (0.001 mol) of DSC in 10 ml of DMF was stirred at ambient temperature. After silica gel TLC. showed that Z-Ala disappeared in the solution, the reaction solution was admixed with a solution of 0.165 g (0.001 mol) of phenylalanine (Phe-OH) and 0.101 g (0.001 mol) of triethylamine in 20 ml of DMF. After 24 hours, the reaction mixture was admixed with ethyl acetate, washed with aqueous 4% NaHCO₃, with 1 N-HCl and with a saturated aqueous solution of sodium chloride, followed by drying over anhydrous sodium sulfate. The dried reaction solution was filtered and the filtrate was distilled to remove the solvent, affording a colorless crystalline substance. Recrystallization of this crystalline substance from methylene chloride-ethyl ether gave 0.27 g of Z-Ala-Phe-OH in the form of a colorless crystalline substance. Yield 72%.

(D) A solution of 0.299 g (0.001 mol) of N-benzyloxycarbonylphenylalanine (Z-Phe), 0.08 g (0.001 mol) of pyridine and 0.256 g (0.001 mol) of DSC in 10 ml of acetonitrile was stirred at ambient temperature. After silica gel TLC. showed that Z-Phe (the free acid form) disappeared in the solution, the reaction solution was admixed with 0.075 g (0.001 mol) of glycine (Gly-OH) and 0.101 g (0.001 mol) of triethylamine, followed by stirring at ambient temperature for 24 hours. The resultant reaction mixture was concentrated to a small volume, admixed with ethyl acetate, washed with aqueous 4% NaHCO$_3$, with 1 N-HCl and with a saturated aqueous solution of sodium chloride, followed by drying over anhydrous sodium sulfate. The dried solution was filtered and the filtrate was distilled to remove the solvent, affording a colorless crystalline substance. Recrystallization of this solid substance from ethyl acetate-petroleum ether gave 0.30 g of N-benzyloxycarbonylphenylalanylglycine (Z-Phe-Gly-OH) as a colorless crystalline substance. Yield 83.4%.

A variety of dipeptides were prepared by the same procedure as mentioned above and some physical constants of them are tabulated in Table 4 below.

TABLE 4

| Dipeptide formed | m.p.(°C.) | m.p.(°C.) described in Literature (a)–(f) | IR (cm$^{-1}$, KBr) | | NMR (ppm, CDCl$_3$) | | Elemental analysis | | |
|---|---|---|---|---|---|---|---|---|---|
| Z—Ala—Phe—OH | 122–125 | 122(a) 124–126(b) | 3200 1710 1640 | $>$NH —OCONH— —CONH— | 1.24 2.92–3.23 3.90–4.46 4.60–5.15 5.08 5.53–6.00 6.80 7.16–7.32 9.67 | (3H.d.-CH$_3$) (2H.m.-CH$_2$) (1H.m.-CH—) (1H.m.-CH—Phe) (2H.s.-CH$_2$—Z) (1H.b.-NH—) (1H.bd.-NH—amide) (10H.two s.-C$_6$H$_5$ × 2) (1H.s.COOH) | Calcd. for C$_{20}$H$_{22}$O$_5$N$_2$ H C N | 5.99% 64.85% 7.56% | Found 6.00% 64.98% 7.44% |
| Z—Ala—Ala—OH | 153–155 | 152–153(c) 148–150(d) | 3300 1700 1650 1520 | $>$NH —OCONH— —CONH— —C$_6$H$_5$ | [CDCl$_3$—CD$_3$OD, 1:1] 1.35,1.40 4.00–4.60 5.13 7.37 | (6H.two d.CH$_3$ × 2) (2H.m.-CH— × 2) (2H.s.-CH$_2$—Z) (5H.s.-C$_6$H$_5$) | Calcd. for C$_{14}$H$_{18}$O$_5$N$_2$ H C N | 6.16% 57.14% 9.52% | Found 6.09% 57.06% 9.40% |
| Z—Ala—Gly—OH | 128–130 | 132(e) | 3300 1700 1650 1520 | $>$NH —OCONH— —CONH— —C$_6$H$_5$ | [CDCl$_3$—CD$_3$OD, 1:1] 1.40 3.98 3.90–4.50 5.14 7.38 | (3H.d.-CH$_3$) (2H.s.-CH$_2$—) (1H.b.-CH—) (2H.s.-CH$_2$—Z) (5H.s.-C$_6$H$_5$) | Calcd. for C$_{13}$H$_{16}$O$_5$N$_2$ H C N | 5.75% 55.71% 9.99% | Found 5.68% 54.41% 9.89% |
| Z—Gly—Leu—OH | 98–100 | 100–102(f) | 3300 1710 1650 | $>$NH —OCONH— —NHCO— | 0.85 1.56 3.87 4.30–5.83 5.07 6.13 7.12 7.30 10.38 | (6H.d.-CH$_3$ × 2) (3H.b.-CH$_2$CH—) (2H.bd.-CH$_2$—) (1H.b.-CH—) (2H.s.-CH$_2$—Z) (1H.b.-NH—) (1H.b.-NH—amide) (5H.s.-C$_6$H$_5$) (1H.s.-COOH) | Calcd. for C$_{16}$H$_{22}$O$_5$N$_2$ H C N | 6.87% 59.61% 8.69% | Found 6.89% 59.61% 8.58% |
| Z—Gly—Pro—OH | 152–155 | | 3300 1710 | $>$NH —OCONH— | 2.80 3.50 3.77–4.15 4.20–4.68 5.13 5.90 7.33 8.38 | (4H.b.-CH$_2$CH$_2$—) (2H.bm.-NCH$_2$—Pro) (2H.bd.-CH$_2$—) (1H.b.-CH—) (2H.s.-CH$_2$—Z) (1H.b.-NH—) (5H.s.-C$_6$H$_5$) (1H.s.-COOH) | Calcd. for C$_{15}$H$_{18}$O$_5$N$_2$ H C N | 5.92% 58.82% 9.15% | Found 5.86% 58.52% 9.01% |
| Z—Phe—Gly—OH | 148.5–150 | | 3320 1740 | $>$NH —OCONH— | [CD$_3$COCD$_3$—d$_6$] 3.18 3.98 4.26–4.72 5.00 5.66–6.18 6.18–6.68 7.30 7.50–7.80 | (2H.d.-CH$_2$—) (2H.d.-CH$_2$—Gly) (1H.b.-CH—) (2H.s.-CH$_2$—Z) (1H.b.-NH—) (1H.b.-NH—amide) (5H.s.-C$_6$H$_5$) (1H.b.-COOH) | Calcd. for C$_{19}$H$_{20}$O$_5$N$_2$ H C N | 5.66% 64.10% 7.77% | Found 5.69% 64.10% 7.77% |

TABLE 4-continued

| Dipeptide formed | m.p.(°C.) | m.p.(°C.) described in Literature (a)-(f) | IR (cm$^{-1}$, KBr) | | NMR (ppm; CDCl$_3$) | | Elemental analysis |
| --- | --- | --- | --- | --- | --- | --- | --- |
| Boc—Phe—Val—OH | | | 3300 | >NH | 0.90 | (6H.dd.-CH$_3$ × 2) | |
| | | | 1730 | >C=O | 1.80-2.46 | (1H.b.-CH—) | |
| | | | 1710 | —OCONH— | 3.03 | (2H.d.-CH$_2$—) | |
| | | | 1650 | —NHCO— | 4.32-4.66 | (2H.m.-CH— × 2) | |
| | | | | | 5.28-5.55 | (1H.m.-NH—) | |
| | | | | | 6.64 | (1H.m.-NH—amide) | |
| | | | | | 7.21 | (5H.s.-C$_6$H$_5$) | |

Notes:
Literature [a]: S. C. J. Fu, S. M. Birnbaum and J. P. Greenstein, "J. Amer. Chem. Soc.", 76, 6054 (1954).
Literature [b]: M. A. Barton, R. U. Lemieux and J. Y. Savaie, "J. Amer, Chem. Soc.", 95, 4501 (1973).
Literature [c]: W. H. Stein, S. Moore and M. Bergmann, "J. Biol. Chemistry", 154, 191 (1944).
Literature [d]: H. R. Boschard, I. Schechter and A. Berger, "Helv. Chim. Acta.", 56, 717 (1973).
Literature [e]: A. Ali, R. M. Cook and B. Weinstein, "Int. J. Peptide Protein Res.", 4, 177 (1972). G. R. Pettit, "Synthetic Peptides.", 125, Elsvier., Amsterdam, (1976).
Literature [f]: H. R. Kricheldorf, Justns Libigs, "Ann. Chem.", 763, 17 (1972).

EXAMPLE 7

This Example illustrates the use of N,N'-disuccinimidyl carbonate (Compound A), N,N'-di-phthalimidyl carbonate (Compound B) and N,N'-bis (5-norobornene-2,3-dicarboximidyl) carbonate (Compound C) as the reagent for forming the active esters of amino acid. The compound A, B or C (0.001 mol) was reacted with 0.001 mol of the respective N-protected amino acids indicated in Table 5 below, in a similar way to the Example 4 to prepare the active ester of the amino acid employed. The yields (%) of the active esters obtained are summarized in Table 5 below.

TABLE 5

| N-Protected amino acid | Yield of Active Esters | | |
| --- | --- | --- | --- |
| | Compound A | Compound B | Compound C |
| Z—Val | 100% | 100% | 100% |
| Z—Pro | 98% | 100% | 99% |
| Z—Met | 100% | 97% | 97% |
| Z—Phe | 100% | 94% | 100% |
| Boc—Phe | 100% | 100% | 100% |

All the active esters which were thus formed by reacting Z-Val, Z-Pro, Z-Met, Z-Phe or Boc-Phe with the carbonate compound A, B or C was entirely identical to those disclosed in the literatures, respectively, with regard to their melting point, elemental analysis and NMR spectrum.

EXAMPLE 8

This example illustrates the reaction of DSC with an amine to produce a urea derivative with the introduction of a carbonyl group.

Cyclohexylamine (198 mg; 0.002 mol) was dissolved in 20 ml of acetonitrile, to which was then added 256 mg (0.001 mol) of DSC. The resultant admixture was stirred at room temperature immediately to deposit dicyclohexylurea. mp. 230°~231° C. Yield 100%. IR. spectrum (cm$^{-1}$): $\nu_{max}^{KBr}$: 3300 (amide), 2900 (CH), 1620 (amide).

EXAMPLE 9

This example illustrates the reaction of DSC with a diamine to produce a hetero-cyclic compound with the introduction of a carbonyl group.

A solution of o-phenylenediamine (108 mg., 0.001 mol) in 100 ml of acetonitrile was stirred at room temperature, to which a solution of 256 mg (0.001 mol) of DSC in 30 ml of acetonitrile was dropwise added over 1.5 hours. After stirring for 3 hours, the reaction mixture was distilled to remove the solvent, and the crystalline material deposited was washed with water to remove the liberated N-hydroxysuccinimide therefrom. Recrystallisation of the crystalline material from methanol-ethyl ether gave 2-hydroxybenzimidazole (as a product of rearrangement of benzphthalimide) in a yield of 88%. mp. more than 300° C.

EXAMPLE 10

This example illustrates the reaction of DSC with dithiocarbamic acid compound to produce an isocyanate compound.

Cyclohexylamine (99 mg, 0.001 mol) and 101 mg (0.001 mol) of triethylamine together with 76 mg (0.001 mol) of carbon disulfide were dissolved in 10 ml of acetonitrile to prepare a solution of cyclohexyldithiocarbamic acid triethylamine salt in acetonitrile. To this solution was added 256 mg (0.001 mol) of DSC and the admixture was stirred for 24 hours at room temperature. The reaction mixture is distilled to remove the acetonitrile and the residue was admixed with ethyl acetate, washed with 1 N-HCl, with aqueous 4% NaHCO$_3$, with water and finally with saturated aqueous NaCl, followed by drying over anhydrous sodium sulfate. The resulting solution was distilled to remove the ethyl acetate and the residue was purified by column-chromatography on silica gel developed with hexane-benzene to give cyclohexylisothiocyanate in a yield of 85%.

EXAMPLE 11

This example illustrates the dehydrating effect of DSC.

A solution of 0.239 g (0.001 mol) of N-benzyloxycarbonylserine (Z-Ser), 0.202 g (0.02 mol) of triethylamine and 0.512 g (0.002 mol) of DSC in 10 ml of acetonitrile was stirred for 2 hours at ambient temperature. The reaction mixture was concentrated and admixed with a volume of ethyl acetate, followed by washing with aqueous 4% NaHCO$_3$, with 1 N-HCl and with saturated aqueous NaCL and further drying over anhydrous sodium sulfate. The solution so dried was distilled to remove the solvent and the residue was purified by column-chromatography on silica gel developed with benzene-chloroform (70:30) to give succinimidyl 2-benzyloxycarbonylamino-propenate. Yield 0.672 g (100%).

EXAMPLE 12

This example illustrates the synthesis of sulpiride with using as the condensation reagent N-succinimidyl diphenylphosphate (SDPP) which is prepared from N-hydroxysuccinimide (HOSu) and diphenylphospholy chloride.

A solution of 462 mg (0.002 mol) of 2-methoxy-5-aminosulfonylbenzoic acid and 256 mg (0.002 mol) of N-ethyl-2-aminomethylpyrrole in 10 ml of acetonitrile was admixed with 694 mg (0.002 mol) of SDPP and 202 mg (0.002 mol) of triethylamine, and the admixture was stirred overnight at room temperature. The crystalline material deposited was collected by filtration and washed with acetonitrile and then with ethanol to give sulpiride, that is, 5-(aminosulfonyl)-N-[(1-ethyl-2-pyrrolidinyl) methyl]-2-methoxybenzamide. mp. 182°~185° C. Yield 24%.

EXAMPLE 13

This example illustrates the synthesis of nicotinic acid dl-α-tocopherol with using SDPP as the active ester-forming reagent.

A solution of 123 mg (0.01 mol) of nicotinic acid, 0.2 ml of triethylamine and 347 mg (0.001 mol) of SDPP in 10 ml of acetonitrile was stirred for 3 hours at room temperature and then admixed with 430 mg (0.001 mol) of dl-α-tocophenol and 152 mg (0.001 mol) of DBU (1,5-diazabicyclo [5.4.0] undec-5-ene). The admixture was refluxed for 13 hours, and the reaction mixture was then distilled to remove the solvent. The syrup residue was admixed with chloroform and washed with water, followed by drying over anhydrous sodium sulfate. The dried solution so obtained was distilled to remove the solvent, and the residue was purified by column-chromatography on silica gel developed with benzene. The nicotinic acid dl-α-tocopherol was obtained as an oil which was coincident with the authentic sample thereof with respect to their IR.spectrum and silica gel thin-layer chromatogram. Nicotinic acid dl-α-tocopherol is known as the drug for lowering the cholesterol level in blood.

What we claim is:

1. A carbonate compound of the formula (I)

wherein R represents a succinimido, phthalimido or 5-norbornene-2,3-dicarboximido group.

2. The carbonate compound of claim 1 which is N,N'-disuccinimidyl carbonate.

3. The carbonate compound of claim 1 which is N,N'-diphthalimidyl carbonate.

4. The carbonate compound of claim 1 which is N,N'-bis (5-norbornene-2,3-dicarboximidyl) carbonate.

* * * * *